United States Patent [19]

Steffen

[11] Patent Number: 5,415,494
[45] Date of Patent: May 16, 1995

[54] PROCESS FOR DETERMINING AND INDICATING THE DEGREE OF GROUND COMPACTING ATTAINED DURING WORK WITH A GROUND COMPACTER

[75] Inventor: Michael Steffen, Gauting, Germany

[73] Assignee: Wacker-Werke GmbH & Co. KG, München, Germany

[21] Appl. No.: 185,838
[22] PCT Filed: Jul. 13, 1992
[86] PCT No.: PCT/EP92/01586
§ 371 Date: Mar. 17, 1994
§ 102(e) Date: Mar. 17, 1994
[87] PCT Pub. No.: WO93/02253
PCT Pub. Date: Feb. 4, 1993

[30] Foreign Application Priority Data

Jul. 20, 1991 [DE] Germany .......... 41 24 193.2

[51] Int. Cl.⁶ .......... E01C 19/30
[52] U.S. Cl. .......... 404/72; 404/133.05
[58] Field of Search .......... 404/72, 117, 133.05, 404/121

[56] References Cited

U.S. PATENT DOCUMENTS 4,411,081 10/1983 King .......... 404/121

5,109,730 5/1992 Zahn et al. .......... 475/256 X

FOREIGN PATENT DOCUMENTS 0092484 10/1983 European Pat. Off. .
0281683 9/1988 European Pat. Off. .
3096637 7/1991 Japan .

Primary Examiner—William P. Neuder
Attorney, Agent, or Firm—Robert W. Becker & Associates

[57] ABSTRACT

A method of determining and displaying during operation an actual degree of soil compaction achieved with a soil compacting device includes the steps of driving the soil compaction device with a motor and compacting the soil with the soil compacting device. The motor is secured against surpassing a predetermined maximum rpm limit by providing a protective rpm limiting circuit. The ignition impulse is delayed with the protective rpm limiting circuit, when the predetermined maximum rpm limit is surpassed. Within a time interval the average of the delay of the ignition impulse is determined as a base value for a display value of the actual degree of compaction. For a large surface area to be compacted it is possible to compact the soil within a test portion to the desired degree of compaction and save the corresponding display value as a reference value to be used during compaction of the remaining portions.

4 Claims, 2 Drawing Sheets

PROCESS FOR DETERMINING AND INDICATING THE DEGREE OF GROUND COMPACTING ATTAINED DURING WORK WITH A GROUND COMPACTER

BACKGROUND OF THE INVENTION

The present invention relates to a method according to a method for determining and displaying the soil compaction attained by working with a soil compacting device.

Soil compacting devices are in general operated with a constant position of the supply control lever, i.e., of the lever controlling the supply of energy.

It is known to monitor a motor parameter that reflects on the load condition of the motor for a real time determination and real time display of the degree of soil compaction attained during working with a soil compacting device, and to convert the parameter to a corresponding electrical signal. Suitable operating parameters for combustion engines in this context are, for example, the torque transmitted by the motor shaft and the load condition of the motor.

The direct determination of the corresponding operating parameters with good precision, especially within the most interesting final range of the desired degree of compaction, however has been difficult in the past and required a great constructive expenditure.

Today, compacting devices are commonly driven by motors which are provided with a protective rpm limiting device.

It is an object of the invention to provide a method of the aforementioned kind which can be performed with relatively small constructive expenditure and which provides very exact results especially in the final range of the desired soil compaction, that is in s range where the decision has to be made whether to cease further soil compaction.

SUMMARY OF THE INVENTION

The method of determining and displaying during operation an actual degree of soil compaction achieved with a soil compacting device according to the present invention is primarily characterized by the following steps:
driving the soil compaction device with a motor;
compacting the soil with the soil compacting device;
securing the motor against surpassing a predetermined maximum rpm limit by providing a protective rpm limiting circuit;
delaying an ignition impulse with the protective rpm limiting circuit, when the predetermined maximum rpm limit is surpassed; and
determining within a time interval the average of the delay of the ignition impulse as a base value for a display value of the actual degree of compaction.

In another embodiment of the present invention a method of compacting large areas of identical soils with a soil compacting device is presented and primarily characterized by the following steps:
a) driving the soil compaction device with a motor;
b) compacting the soil with the soil compacting device on a portion of the large area to be compacted to a desired degree of compaction;
c) securing the motor against surpassing a predetermined maximum rpm limit by providing a protective rpm limiting circuit;
d) delaying an ignition impulse with the protective rpm limiting circuit, when the predetermined maximum rpm limit is surpassed;
e) determining within a time interval the average of the delay of the ignition impulse as a base value for a display value of the actual degree of compaction;
f) employing the display value at the desired degree of compaction as a reference value for the compaction of the remaining portions of the large area to be compacted;
g) repeating steps b) to e) for the remaining portions of the large area to be compacted; and
h) terminating the compacting operation on the remaining portions of the large surface area to be compacted when the display value of the actual degree of compaction reaches the reference value.

Preferably, the reference value is saved and displayed constantly together with the display value of the actual degree of compaction.

Advantageously, for determining the reference value in step b) the soil is compacted to a maximum attainable degree of compaction.

The control parameter for the control system, respectively, the degree of its activity, are no direct operating parameters of the motor, however, they reflect the actual load condition of the motor especially at the end of the compaction operation of a soil area currently being compacted in a very exact manner and can be converted in an especially simple manner into a corresponding electric signal.

DESCRIPTION OF PREFERRED EMBODIMENTS

Figure 1:
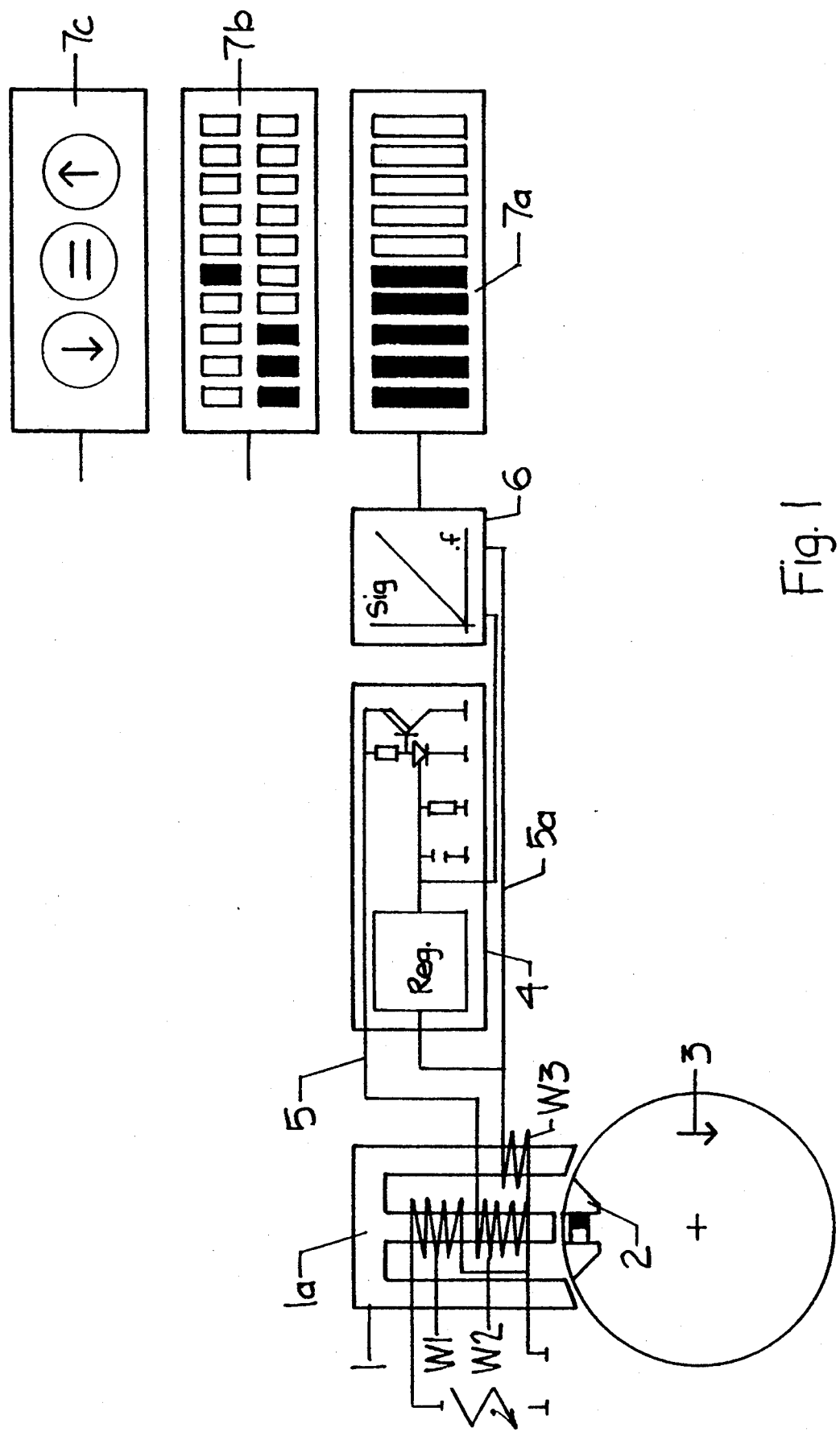

The invention will be explained in the following with the aid of the drawing representing two embodiments in connection with soil compacting devices which are driven by external auto-ignited combustion engines.

It is shown in: FIG. 1 a device for performing the inventive method in connection with an external auto-ignited drive motor by sensing the ignition impulses of a rpm-limited drive motor, and FIG. 2 a device for performing the method in connection with an external auto-ignited drive motor that is prevented from surpassing the maximum rpm value by delaying the ignition impulse.

DESCRIPTION OF PREFERRED EMBODIMENTS

In the drawing only the electronic ignition circuit with the parts driven by the motor are schematically represented as well as the device for sensing the activity of the control system and for transforming the activity to a corresponding display signal. The motor which is not shown in detail is of a conventional design.

The compaction device driven by the motor may be a compaction plate, a ram, a roller etc. of known construction.

In the embodiment represented in FIG. 1 of the drawing the ignition device for the motor is provided with an ignition transformer 1 having an E-core $1a$ which on two of the three core legs is provided with three coils W1, W2, and W3. The legs of the magnet core $1a$ are bridged on their end face periodically in pairs with a yoke 2 passing sequentially the legs, which yoke 2 rotates synchronously with the cam shaft in the direction indicated with arrow 3. The coils W1 and W2 are arranged on the central leg, the coil W3 is positioned on the outermost rearward leg in the rotational direction of the yoke 2.

The coil W1 is the high voltage secondary coil for loading the respective spark plug, optionally via a nonrepresented distributor, and the coil W2 is the corresponding primary coil which is loaded by the electronic ignition circuit 4. The coil W3 supplies the ignition electronic 4 with a rpm-proportional electric signal. The electronic ignition circuit 4 provides for a rpm limitation according to the principle of the so-called intermittent control, i.e., it loads the coil W2 with a number of ignition impulses corresponding to the rpm value of the cam shaft at the right ignition time only when this rpm value does not surpass a predetermined limit. The corresponding rpm value can only be surpassed to a small amount because the electronic ignition circuit 4 omits increasingly ignition impulses for the coil W2 with respect to the signal received from the coil W3. The difference between the pulse frequency of the pulse which is sent via the ignition electronic 4 and the line 5a from the coil W3 and the pulse frequency of the pulse of the line 5 from the electronic ignition circuit 4 to the coil W2 is thus a measure for the activity of the control system for the rpm limitation. The aforementioned pulses are entered into an electronic subtractor 6 which generates a signal in the form of a dc voltage corresponding to the pulse frequency difference which dc voltage is displayed with a voltage display 7a in the field of vision of the operator of the compacting device as a value for the actual degree of compaction. The dc voltage represents a reference value for the corresponding achieved degree of compaction because with the increasing degree of compaction the load of the motor becomes smaller so that the rpm value for a constant position of the supply degree lever is bound to increase.

Figure 2:
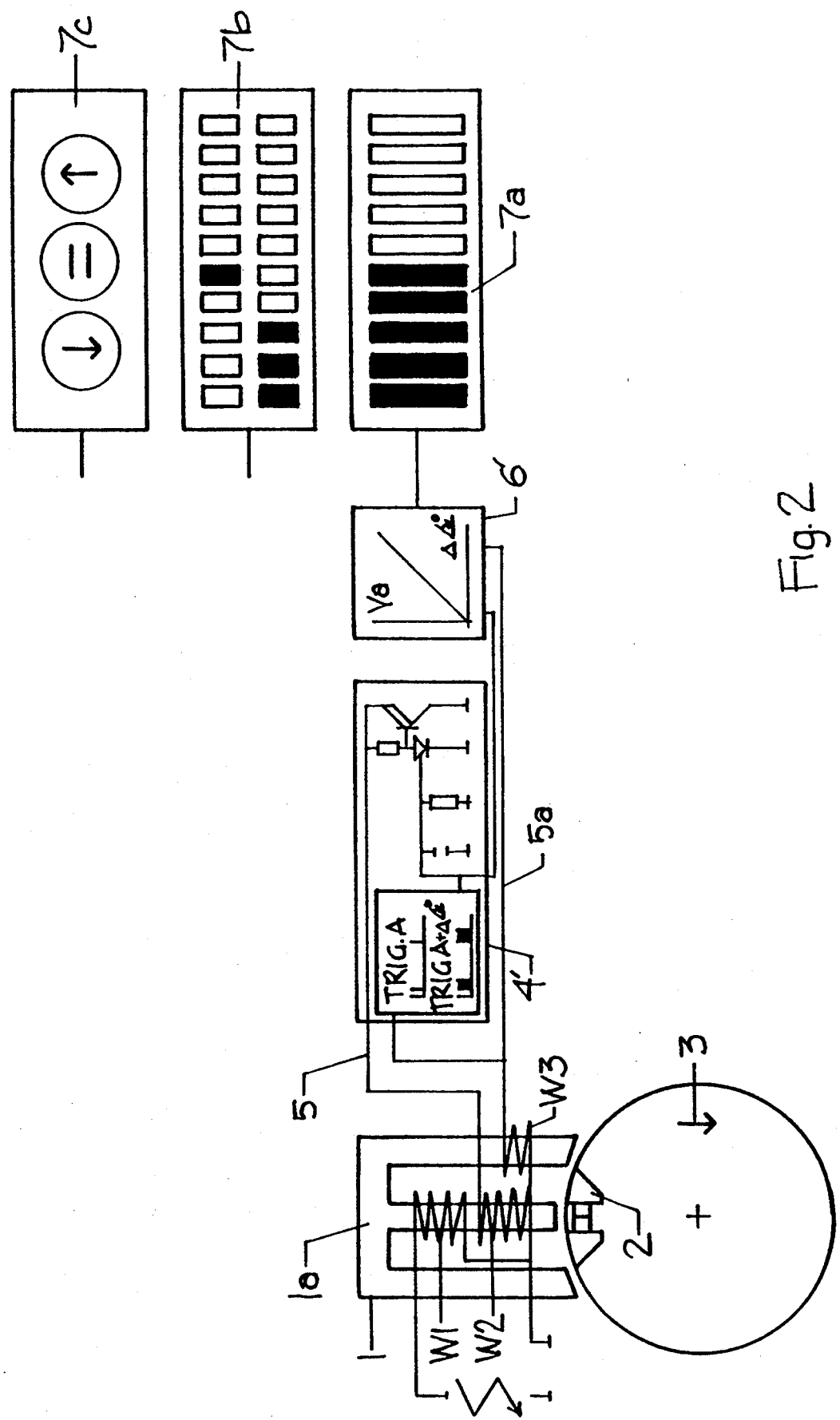

The embodiment according to FIG. 2 differs from the embodiment of FIG. 1 in that the electronic ignition circuit 4' is designed such that it supplies a number of ignition impulses corresponding to the rpm value of the cam shaft to the spark plugs, but delays the ignition point progressively when approaching the maximum rpm value. The pulse supplied by the coil W3 and, on the other hand, the pulse generated by the electronic ignition circuit 4' to the spark plugs is guided to the computer 6', but in the present embodiment the computer 6' provides a dc voltage which corresponds to the average value of the phase displacement of the two pulses for a predetermined time interval, i.e., the average value of the delay changing from time interval to time interval, which thus reflects the activity of the control system. The dc voltage in this case is thus also a measure for the attained degree of compaction.

The dc voltage as shown in the embodiment according to FIG. 1 is displayed on a voltage display 7a.

Of course, in both embodiments the electronic ignition circuit 4, respectively, 4' contains in addition to the actual rpm value further information which is important for the ignition point of the motor, for example, the suction pressure within the suction tube and the engine temperature.

When, as is the case for a simple voltage display 7a in FIG. 1 and in FIG. 2, only the actual activity of the control system is displayed, the operator must constantly monitor the activity display at the end of the compacting operation in order to determine when the maximum degree of soil compaction has been reached, which the operator can determine based on the activity of the control system and thus its display, for example, at the voltage display 7a, remaining unchanged. Depending on the type of soil to be compacted, the activity of the control system in the achievable end condition of soil compaction may vary so that this end condition is not necessarily reflected in a predetermined display value. It is often the case that larger areas of one and the same type of soil must be compacted and that the operator must determine over the entire surface area, respectively, for each portion of the surface area which he works on individually and of which portions the entire surface area is composed, the state at which the activity is no longer changing, thus indicating the maximum soil compaction, by continuously monitoring the changes of the displayed actual activity. This requires the full attention of the operator for a respectively long time period. This determination can be substantially simplified for the operator when he is given the possibility to perform for an individual, relatively small part of the entire surface area the aforementioned observations, to save the activity value for this portion, and to display this value as a reference value. For the remaining portion of soil compaction over the entire surface area the operator then only needs to compare the displayed actual control system activity to the reference value and can terminate the compacting operation when the actual display corresponds to the reference value. This simplifies the monitoring of the compacting operation substantially and thus requires less attention.

In FIG. 1 and FIG. 2 above the voltage display 7a two alternative display devices 7b and 7c are represented. Each can be used instead of the voltage supply 7a and makes possible the aforementioned method. The display device 7b displays, as does the voltage display 7a, in the form of a bar in the upper half the saved reference value of the control system activity for the previously performed compaction of a test portion of the entire area to be compacted and having the same type of soil and in the row below the actual activity degree of the control system of the further compaction. In the shown embodiment, the compaction for a portion or for the entire area is to be terminated when the last one of the black bars in the lower row is below the black bar in the upper row.

The display device 7c is a comparative display functioning as a window discriminator that operates with three LEDs or CCDs that during the course of the compacting operation will light up sequently, whereby, =, means: less/same/higher soil compaction as in the final state of the testing area.

The display of the display devices 7b and 7c is based, as is the voltage supply 7a in FIG. 1, on the load degree of the ignition impulses and in FIG. 2 on the delay displacement angle.

In cases in which the operator knows the type of soil with respect to its behavior and its properties during compaction it is also possible to provide means for entering, saving, and the separate permanent display of a reference value selected by the operator according to his experience.

The present invention is, of course, in no way restricted to the specific disclosure of the specification and drawings, but also encompasses any modifications within the scope of the appended claims.

I claim:

1. A method of determining and displaying during operation an actual degree of soil compaction achieved with a soil compacting device, said method comprising the steps of:

driving the soil compaction device with a motor;

compacting the soil with the soil compacting device;

securing the motor against surpassing a predetermined maximum rpm limit by providing a protective rpm limiting circuit;

delaying an ignition impulse with the protective rpm limiting circuit, when the predetermined maximum rpm limit is surpassed; and determining within a time interval the average of the delay of the ignition impulse as a base value for a display value of the actual degree of compaction.

2. A method of compacting large areas of identical soils with a soil compacting device, said method comprising the steps of:

a) driving the soil compaction device with a motor;

b) compacting the soil with the soil compacting device on a portion of the large area to be compacted to a desired degree of compaction;

c) securing the motor against surpassing a predetermined maximum rpm limit by providing a protective rpm limiting circuit;

d) delaying an ignition impulse with the protective rpm limiting circuit, when the predetermined maximum rpm limit is surpassed;

e) determining within a time interval the average of the delay of the ignition impulse as a base value for a display value of the actual degree of compaction;

f) employing the display value at the desired degree of compaction as a reference value for the compaction of the remaining portions of the large area to be compacted;

g) repeating steps b) to e) for the remaining portions of the large area to be compacted; and h) terminating the compacting operation on the remaining portions of the large surface area to be compacted when the display value of the actual degree of compaction reaches the reference value.

3. A method according to claim 2, further comprising the steps of saving the reference value and displaying the reference value constantly together with the display value of the actual degree of compaction.

4. A method according to claim 2, wherein for determining the reference value in said step b) the soil is compacted to a maximum attainable degree of compaction.

* * * * *